United States Patent
Govari et al.

(10) Patent No.: US 12,011,280 B2
(45) Date of Patent: Jun. 18, 2024

(54) ELECTROPHYSIOLOGICAL MAPPING IN THE PRESENCE OF INJURY CURRENT

(71) Applicant: Biosense Webster (Israel) Ltd., Yokneam (IL)

(72) Inventors: Assaf Govari, Haifa (IL); Andres Claudio Altmann, Yokneam (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 256 days.

(21) Appl. No.: 17/492,933

(22) Filed: Oct. 4, 2021

(65) Prior Publication Data

US 2023/0106727 A1   Apr. 6, 2023

(51) Int. Cl.
| | | |
|---|---|---|
| A61B 5/367 | (2021.01) | |
| A61B 5/00 | (2006.01) | |
| A61B 5/256 | (2021.01) | |
| A61B 5/283 | (2021.01) | |
| A61B 5/339 | (2021.01) | |

(52) U.S. Cl.
CPC .............. *A61B 5/367* (2021.01); *A61B 5/256* (2021.01); *A61B 5/283* (2021.01); *A61B 5/339* (2021.01); *A61B 5/7221* (2013.01); *A61B 5/7225* (2013.01)

(58) Field of Classification Search
None
See application file for complete search history.

(56) References Cited

U.S. PATENT DOCUMENTS

| | | | | |
|---|---|---|---|---|
| 4,681,117 | A | * | 7/1987 | Brodman ............... A61B 5/283 600/374 |
| 4,699,147 | A | | 10/1987 | Chilson et al. |
| 4,940,064 | A | | 7/1990 | Desai |
| 5,215,103 | A | | 6/1993 | Desai |
| 5,255,679 | A | | 10/1993 | Imran |
| 5,293,869 | A | | 3/1994 | Edwards et al. |
| 5,309,910 | A | | 5/1994 | Edwards et al. |
| 5,313,943 | A | | 5/1994 | Houser et al. |
| 5,324,284 | A | | 6/1994 | Imran |
| 5,345,936 | A | | 9/1994 | Pomeranz et al. |
| 5,365,926 | A | | 11/1994 | Desai |
| 5,396,887 | A | | 3/1995 | Imran |
| 5,400,783 | A | | 3/1995 | Pomeranz et al. |
| 5,411,025 | A | | 5/1995 | Webster, Jr. |
| 5,415,166 | A | | 5/1995 | Imran |

(Continued)

FOREIGN PATENT DOCUMENTS

| | | |
|---|---|---|
| CN | 111248993 A | 6/2020 |
| CN | 111248996 A | 6/2020 |

(Continued)

OTHER PUBLICATIONS

Extended European Search Report dated Feb. 2, 2023, from corresponding European Application No. 22199328.0.

*Primary Examiner* — Kennedy Schaetzle
(74) *Attorney, Agent, or Firm* — Troutman Pepper Hamilton Sanders LLP

(57) ABSTRACT

A system includes an interface and a processor. The interface is configured to receive an electrogram acquired in a heart of a patient. The processor is configured to (i) estimate a level of injury current present in the electrogram, and (ii) based on the estimated level of injury current, decide whether to use the electrogram in a subsequent analysis.

24 Claims, 3 Drawing Sheets

(56) References Cited

U.S. PATENT DOCUMENTS

| | | |
|---|---|---|
| 5,456,254 A | 10/1995 | Pietroski et al. |
| 5,465,717 A | 11/1995 | Imran et al. |
| 5,476,495 A | 12/1995 | Kordis et al. |
| 5,499,981 A | 3/1996 | Kordis |
| 5,526,810 A | 6/1996 | Wang |
| 5,546,940 A | 8/1996 | Panescu et al. |
| 5,549,108 A | 8/1996 | Edwards et al. |
| 5,558,073 A | 9/1996 | Pomeranz et al. |
| 5,577,509 A | 11/1996 | Panescu et al. |
| 5,595,183 A | 1/1997 | Swanson et al. |
| 5,598,848 A | 2/1997 | Swanson et al. |
| 5,609,157 A | 3/1997 | Panescu et al. |
| 5,628,313 A | 5/1997 | Webster, Jr. |
| 5,681,280 A | 10/1997 | Rusk et al. |
| 5,722,401 A | 3/1998 | Pietroski et al. |
| 5,722,403 A | 3/1998 | McGee et al. |
| 5,725,525 A | 3/1998 | Kordis |
| 5,730,128 A | 3/1998 | Pomeranz et al. |
| 5,772,590 A | 6/1998 | Webster, Jr. |
| 5,782,899 A | 7/1998 | Imran |
| 5,823,189 A | 10/1998 | Kordis |
| 5,881,727 A | 3/1999 | Edwards |
| 5,893,847 A | 4/1999 | Kordis |
| 5,904,680 A | 5/1999 | Kordis et al. |
| 5,911,739 A | 6/1999 | Kordis et al. |
| 5,928,228 A | 7/1999 | Kordis et al. |
| 5,968,040 A | 10/1999 | Swanson et al. |
| 6,014,579 A | 1/2000 | Pomeranz et al. |
| 6,014,590 A | 1/2000 | Whayne et al. |
| 6,119,030 A | 9/2000 | Morency |
| 6,216,043 B1 | 4/2001 | Swanson et al. |
| 6,216,044 B1 | 4/2001 | Kordis |
| 6,428,537 B1 | 8/2002 | Swanson et al. |
| 6,456,864 B1 | 9/2002 | Swanson et al. |
| 6,574,492 B1 | 6/2003 | Ben-Haim et al. |
| 6,584,345 B2 | 6/2003 | Govari |
| 6,600,948 B2 | 7/2003 | Ben-Haim et al. |
| 6,738,655 B1 | 5/2004 | Sen et al. |
| 6,741,878 B2 | 5/2004 | Fuimaono et al. |
| 6,748,255 B2 | 6/2004 | Fuimaono et al. |
| 6,780,183 B2 | 8/2004 | Jimenez, Jr. et al. |
| 6,837,886 B2 | 1/2005 | Collins et al. |
| 6,866,662 B2 | 3/2005 | Fuimaono et al. |
| 6,892,091 B1 | 5/2005 | Ben-Haim et al. |
| 6,970,730 B2 | 11/2005 | Fuimaono et al. |
| 6,973,340 B2 | 12/2005 | Fuimaono et al. |
| 6,980,858 B2 | 12/2005 | Fuimaono et al. |
| 7,048,734 B1 | 5/2006 | Fleischman et al. |
| 7,149,563 B2 | 12/2006 | Fuimaono et al. |
| 7,255,695 B2 | 8/2007 | Falwell et al. |
| 7,257,434 B2 | 8/2007 | Fuimaono et al. |
| 7,399,299 B2 | 7/2008 | Daniel et al. |
| 7,410,486 B2 | 8/2008 | Fuimaono et al. |
| 7,522,950 B2 | 4/2009 | Fuimaono et al. |
| RE41,334 E | 5/2010 | Beatty et al. |
| 7,846,157 B2 | 12/2010 | Kozel |
| 7,930,018 B2 | 4/2011 | Harlev et al. |
| 8,007,495 B2 | 8/2011 | McDaniel et al. |
| 8,048,063 B2 | 11/2011 | Aeby et al. |
| 8,103,327 B2 | 1/2012 | Harlev et al. |
| 8,167,845 B2 | 5/2012 | Wang et al. |
| 8,224,416 B2 | 7/2012 | De La Rama et al. |
| 8,235,988 B2 | 8/2012 | Davis et al. |
| 8,346,339 B2 | 1/2013 | Kordis et al. |
| 8,435,232 B2 | 5/2013 | Aeby et al. |
| 8,447,377 B2 | 5/2013 | Harlev et al. |
| 8,456,182 B2 | 6/2013 | Bar-Tal et al. |
| 8,498,686 B2 | 7/2013 | Grunewald |
| 8,517,999 B2 | 8/2013 | Pappone et al. |
| 8,545,490 B2 | 10/2013 | Mihajlovic et al. |
| 8,560,086 B2 | 10/2013 | Just et al. |
| 8,567,265 B2 | 10/2013 | Aeby et al. |
| 8,712,550 B2 | 4/2014 | Grunewald |
| 8,755,861 B2 | 6/2014 | Harlev et al. |
| 8,825,130 B2 | 9/2014 | Just et al. |
| 8,906,011 B2 | 12/2014 | Gelbart et al. |
| 8,945,120 B2 | 2/2015 | McDANIEL et al. |
| 8,979,839 B2 | 3/2015 | De La Rama et al. |
| 9,037,264 B2 | 5/2015 | Just et al. |
| 9,131,980 B2 | 9/2015 | Bloom |
| 9,204,929 B2 | 12/2015 | Solis |
| 9,277,960 B2 | 3/2016 | Weinkam et al. |
| 9,314,208 B1 | 4/2016 | Altmann et al. |
| 9,339,331 B2 | 5/2016 | Tegg et al. |
| 9,486,282 B2 | 11/2016 | Solis |
| 9,554,718 B2 | 1/2017 | Bar-Tal et al. |
| D782,686 S | 3/2017 | Werneth et al. |
| 9,585,588 B2 | 3/2017 | Marecki et al. |
| 9,597,036 B2 | 3/2017 | Aeby et al. |
| 9,687,297 B2 | 6/2017 | Just et al. |
| 9,693,733 B2 | 7/2017 | Altmann et al. |
| 9,782,099 B2 | 10/2017 | Williams et al. |
| 9,788,895 B2 | 10/2017 | Solis |
| 9,801,681 B2 | 10/2017 | Laske et al. |
| 9,814,618 B2 | 11/2017 | Nguyen et al. |
| 9,833,161 B2 | 12/2017 | Govari |
| 9,894,756 B2 | 2/2018 | Weinkam et al. |
| 9,895,073 B2 | 2/2018 | Solis |
| 9,907,609 B2 | 3/2018 | Cao et al. |
| 9,974,460 B2 | 5/2018 | Wu et al. |
| 9,986,949 B2 | 6/2018 | Govari et al. |
| 9,993,160 B2 | 6/2018 | Salvestro et al. |
| 10,014,607 B1 | 7/2018 | Govari et al. |
| 10,028,376 B2 | 7/2018 | Weinkam et al. |
| 10,034,637 B2 | 7/2018 | Harlev et al. |
| 10,039,494 B2 | 8/2018 | Altmann et al. |
| 10,045,707 B2 | 8/2018 | Govari |
| 10,078,713 B2 | 9/2018 | Auerbach et al. |
| 10,111,623 B2 | 10/2018 | Jung et al. |
| 10,130,420 B2 | 11/2018 | Basu et al. |
| 10,136,828 B2 | 11/2018 | Houben et al. |
| 10,143,394 B2 | 12/2018 | Solis |
| 10,172,536 B2 | 1/2019 | Maskara et al. |
| 10,182,762 B2 | 1/2019 | Just et al. |
| 10,194,818 B2 | 2/2019 | Williams et al. |
| 10,201,311 B2 | 2/2019 | Chou et al. |
| 10,219,860 B2 | 3/2019 | Harlev et al. |
| 10,219,861 B2 | 3/2019 | Just et al. |
| 10,231,328 B2 | 3/2019 | Weinkam et al. |
| 10,238,309 B2 | 3/2019 | Bar-Tal et al. |
| 10,278,590 B2 | 5/2019 | Salvestro et al. |
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,702,178 B2 | 7/2020 | Dahlen et al. |

(56) References Cited

U.S. PATENT DOCUMENTS

| | | |
|---|---|---|
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2004/0133113 A1* | 7/2004 | Krishnan ............... A61B 5/05 600/508 |
| 2004/0210121 A1 | 10/2004 | Fuimaono et al. |
| 2006/0009689 A1 | 1/2006 | Fuimaono et al. |
| 2006/0009690 A1 | 1/2006 | Fuimaono et al. |
| 2006/0100669 A1 | 5/2006 | Fuimaono et al. |
| 2007/0021679 A1 | 1/2007 | Narayan et al. |
| 2007/0093806 A1 | 4/2007 | Desai et al. |
| 2007/0276212 A1 | 11/2007 | Fuimaono et al. |
| 2008/0234564 A1 | 9/2008 | Beatty et al. |
| 2011/0118726 A1 | 5/2011 | De La Rama et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0301597 A1 | 12/2011 | McDaniel et al. |
| 2012/0184864 A1 | 7/2012 | Harlev et al. |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0296852 A1 | 11/2013 | Madjarov et al. |
| 2014/0025069 A1 | 1/2014 | Willard et al. |
| 2014/0052118 A1 | 2/2014 | Laske et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0257069 A1 | 9/2014 | Eliason et al. |
| 2014/0276712 A1 | 9/2014 | Mallin et al. |
| 2014/0309512 A1 | 10/2014 | Govari et al. |
| 2015/0011991 A1 | 1/2015 | Buysman et al. |
| 2015/0045863 A1 | 2/2015 | Litscher et al. |
| 2015/0080693 A1 | 3/2015 | Solis |
| 2015/0105770 A1 | 4/2015 | Amit |
| 2015/0119878 A1 | 4/2015 | Heisel et al. |
| 2015/0133919 A1 | 5/2015 | McDaniel et al. |
| 2015/0208942 A1 | 7/2015 | Bar-Tal et al. |
| 2015/0250424 A1 | 9/2015 | Govari et al. |
| 2015/0270634 A1 | 9/2015 | Buesseler et al. |
| 2015/0342532 A1 | 12/2015 | Basu et al. |
| 2016/0081746 A1 | 3/2016 | Solis |
| 2016/0113582 A1 | 4/2016 | Altmann et al. |
| 2016/0113709 A1 | 4/2016 | Maor |
| 2016/0183877 A1 | 6/2016 | Williams et al. |
| 2016/0228023 A1 | 8/2016 | Govari |
| 2016/0228062 A1 | 8/2016 | Altmann et al. |
| 2016/0278853 A1 | 9/2016 | Ogle et al. |
| 2016/0302858 A1 | 10/2016 | Bencini |
| 2016/0338770 A1 | 11/2016 | Bar-Tal et al. |
| 2017/0027638 A1 | 2/2017 | Solis |
| 2017/0056103 A1* | 3/2017 | Fang ............... A61B 18/1492 |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0156790 A1 | 6/2017 | Aujla |
| 2017/0172442 A1 | 6/2017 | Govari |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0319144 A1 | 11/2017 | Shah et al. |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0008203 A1 | 1/2018 | Iyun et al. |
| 2018/0028084 A1 | 2/2018 | Williams et al. |
| 2018/0049803 A1 | 2/2018 | Solis |
| 2018/0085064 A1 | 3/2018 | Auerbach et al. |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279954 A1 | 10/2018 | Hayam et al. |
| 2018/0296167 A1 | 10/2018 | Stewart et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Mswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |

(56) References Cited

U.S. PATENT DOCUMENTS

| | | |
|---|---|---|
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205739 A1 | 7/2020 | Garrett et al. |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0352465 A1 | 11/2020 | Gaeta |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077022 A1* | 3/2021 | Grinberg ............... A61N 1/372 |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0169421 A1 | 6/2021 | Govari |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0178166 A1 | 6/2021 | Govari et al. |
| 2021/0186363 A1 | 6/2021 | Gliner et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |

FOREIGN PATENT DOCUMENTS

| | | |
|---|---|---|
| EP | 0668740 A1 | 8/1995 |
| EP | 0644738 B1 | 3/2000 |
| EP | 0727183 B1 | 11/2002 |
| EP | 0727184 B1 | 12/2002 |
| EP | 2783651 A1 | 10/2014 |
| EP | 2699151 B1 | 11/2015 |
| EP | 2699152 B1 | 11/2015 |
| EP | 2699153 B1 | 12/2015 |
| EP | 2498706 B1 | 4/2016 |
| EP | 2578173 B1 | 6/2017 |
| EP | 3238645 A1 | 11/2017 |
| EP | 2884931 B1 | 1/2018 |
| EP | 2349440 B1 | 8/2019 |
| EP | 3318211 B1 | 12/2019 |
| EP | 3581135 A1 | 12/2019 |
| EP | 2736434 B1 | 2/2020 |
| EP | 3451962 B1 | 3/2020 |
| EP | 3972510 A1 | 3/2022 |
| WO | 9421167 A1 | 9/1994 |
| WO | 9421169 A1 | 9/1994 |
| WO | 9625095 A1 | 8/1996 |
| WO | 9634560 A1 | 11/1996 |
| WO | 0182814 B1 | 5/2002 |
| WO | 2004087249 A2 | 10/2004 |
| WO | 2012100185 A2 | 7/2012 |
| WO | 2013052852 A1 | 4/2013 |
| WO | 2013162884 A1 | 10/2013 |
| WO | 2013173917 A1 | 11/2013 |
| WO | 2013176881 A1 | 11/2013 |
| WO | 2014176205 A1 | 10/2014 |
| WO | 2016019760 A1 | 2/2016 |
| WO | 2016044687 A1 | 3/2016 |
| WO | 2018111600 A1 | 6/2018 |
| WO | 2018191149 A1 | 10/2018 |
| WO | 2019084442 A1 | 5/2019 |
| WO | 2019143960 A1 | 7/2019 |
| WO | 2020026217 A1 | 2/2020 |
| WO | 2020206328 A1 | 10/2020 |

* cited by examiner

ELECTROPHYSIOLOGICAL MAPPING IN THE PRESENCE OF INJURY CURRENT

FIELD OF THE INVENTION

The present invention relates generally to processing of electrophysiological signals, and specifically to enabling electrophysiological mapping in the presence of signal baseline wander.

BACKGROUND OF THE INVENTION

Various methods to account for electrophysiological signal noise have been proposed in the patent literature. For example, U.S. Patent Application Publication 2007/0021679 describes the analysis of surface electrocardiographic and intracardiac signals to identify and separate electrical activity corresponding to distinct but superimposed events in the heart. The analysis assesses the spatial phase, temporal phase, rate, spectrum and reproducibility of each event to determine uniformity of activation in all spatial dimensions. The analysis uses numerical indices derived from these analyses to diagnose arrhythmias. The analysis uses these indices to determine the location of an arrhythmia circuit, and to direct the movement of an electrode catheter to this location for ablation or permanent catheter positioning. The analysis uses variability in these indices from the surface electrocardiogram to indicate subtle beat-to-beat fluctuations which reflect the tendency towards atrial and ventricular arrhythmias. The analysis is generally performed after baseline correction, which makes the analysis insensitive to noise factors including baseline wander.

SUMMARY OF THE INVENTION

An embodiment of the present invention that is described hereinafter provides a system including an interface and a processor. The interface is configured to receive an electrogram acquired in a heart of a patient. The processor is configured to (i) estimate a level of injury current present in the electrogram, and (ii) based on the estimated level of injury current, decide whether to use the electrogram in a subsequent analysis.

In some embodiments, the processor is configured to use the electrogram when the level of injury current is below a threshold, and to discard the electrogram when the level of injury current is above the threshold.

In some embodiments, the electrogram is a unipolar signal acquired between a reference electrode immersed in blood and a sensing electrode in contact with tissue.

In an embodiment, the processor is configured to estimate the level of injury current by comparing a peak level of the electrogram to a threshold.

In another embodiment, the processor is configured to use the electrogram by annotating the electrogram and using the annotation in an EP map.

In some embodiments, the processor is configured to annotate a local activation time (LAT) value in the electrogram.

There is additionally provided, in accordance with an embodiment of the present invention, a system including an interface and a processor. The interface is configured to receive at least two EP signals acquired in a heart of a patient by a catheter. The processor is configured to (a) using the at least two EP signals, estimate a level of injury current present in an EP signal derived from the at least two EP signals, and (b) based on the estimated level of injury current, decide whether to use the electrogram in a subsequent analysis.

In some embodiments, the processor is configured to derive the EP signal by selecting one of the at least two EP signals.

In some embodiments, one of the at least two EP signals is an electrogram acquired using a reference electrode immersed in blood and a surface electrode, and another of the at least two EP signals is an electrogram acquired using a sensing electrode in contact with tissue and the surface electrode.

In an embodiment, the surface electrode is a WCT terminal.

In another embodiment, the processor is configured to estimate the level of injury current by comparing between at least two of the EP signals.

In some embodiments, the processor is configured to use the derived EP signal by annotating the derived EP signal and using the annotation in an EP map.

In some embodiments, the processor is configured to annotate a local activation time (LAT) value in the derived EP signal.

There is further provided, in accordance with an embodiment of the present invention, a method including receiving an electrogram acquired in a heart of a patient. A level of injury current present in the electrogram is estimated. Based on the estimated level of injury current, it is decided whether to use the electrogram in a subsequent analysis.

There is furthermore provided, in accordance with an embodiment of the present invention, a method including receiving at least two EP signals acquired in a heart of a patient by a catheter. Using the at least two EP signals, a level is estimated, of injury current present in an EP signal derived from the at least two EP signals. Based on the estimated level of injury current, it is decided whether to use the electrogram in a subsequent analysis.

The present invention will be more fully understood from the following detailed description of the embodiments thereof, taken together with the drawings in which:

DETAILED DESCRIPTION OF EMBODIMENTS

Overview

Figure 1:
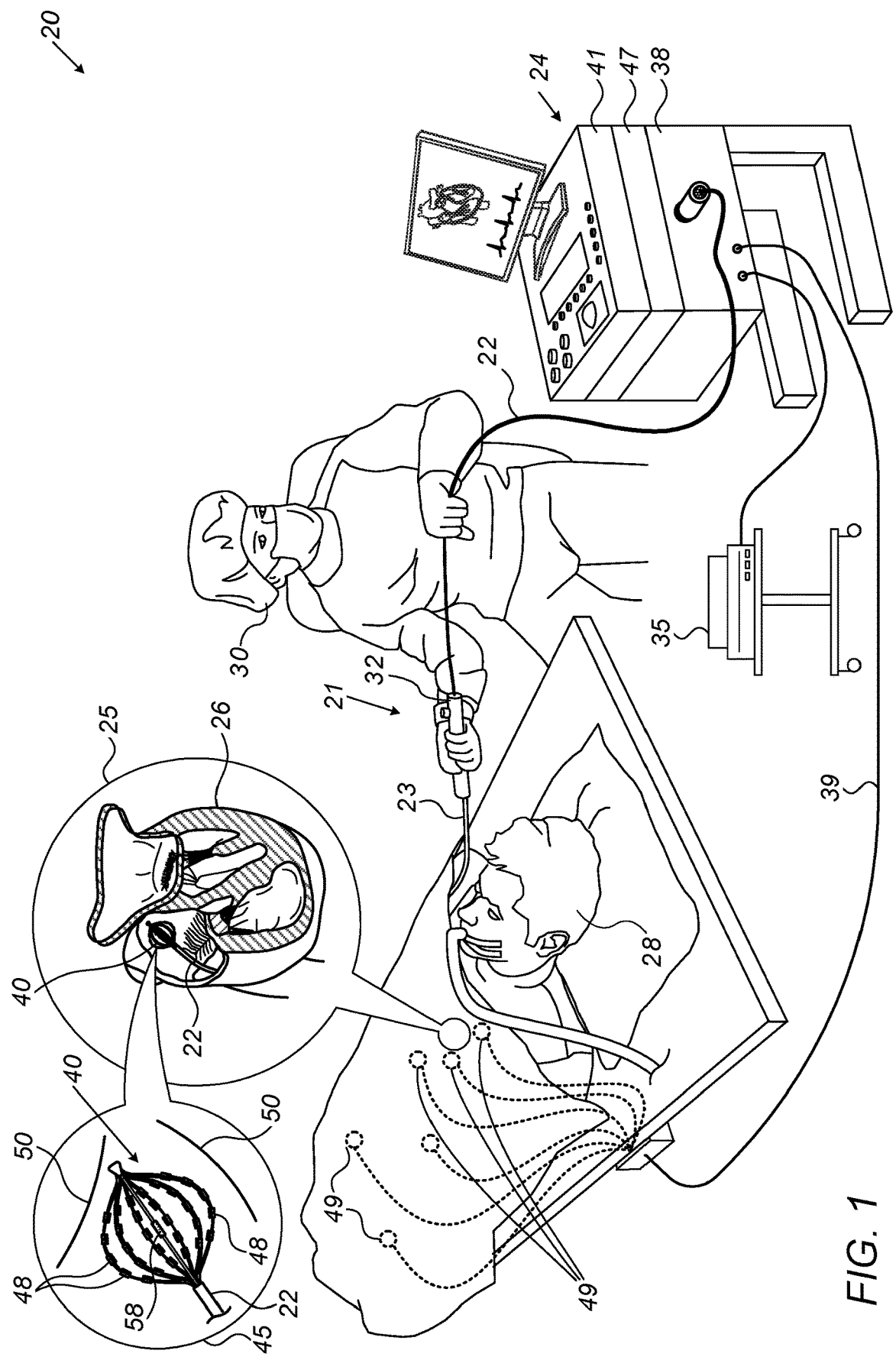
FIG. 1 is a schematic, pictorial illustration of a catheter-based electrophysiological (EP) sensing and signal-analysis system, according to an embodiment of the present invention.

Intracardiac electrophysiological (EP) mapping is a catheter-based method that is sometimes applied to characterize cardiac EP wave propagation abnormalities, such as abnormalities that cause arrhythmia. In a typical catheter-based procedure, a distal end of a catheter, which comprises multiple sensing electrodes, is inserted into the heart to sense a set of data points comprising measured locations over a wall tissue of a cardiac chamber and a respective set of EP signals (e.g., intra-cardiac electrograms (EGM)), from which the EP mapping system can produce an EP map of the cardiac chamber. Further to this, available cardiac data may also include multi-channel (e.g., 12-channel) extra-cardiac electrocardiograms (ECG).

During EP signal acquisition, a well-known signal artifact is the presence of "injury current," which manifests itself as a baseline shift, or baseline wander, due to the presence of very low-frequency components (e.g., DC) in the acquired signal. The injury current is typically caused by the acquiring electrode pushing on cardiac cells, so that the cells, in turn, polarize. It is possible in principle to try and filter-out the injury current by applying a high-pass filter to the signal; however, the filtered signal may still have artifacts that cause errors when the signals are analyzed, such as errors in annotation of late activation time (LAT).

Embodiments of the present invention that are described herein provide methods and systems for detecting and mitigating the effects of injury current in EP mapping procedures. Some disclosed techniques analyze acquired electrograms used for mapping, for detecting the presence of injury current. When injury current is detected in a certain electrogram (also referred to herein simply as "EP signal" or "signal"), e.g., by one of the algorithms described below, the signal is not used for mapping. If there is no detected injury current, the signal is used, for example, by being annotated as an activation in an EP map, such as an LAT map.

In some embodiments, the electrogram signals are acquired using a multi-electrode catheter, such as a basket catheter, which has a central reference electrode. In these implementations, the electrograms are unipolar signals that are measured between the central reference electrode of the basket (which does not contact tissue and is assumed to be a local ground) and a spine electrode in contact with the tissue. In these embodiments, a processor assumes that injury current is present if the acquired signal (typically peak level of the signal) is greater than a preset threshold, for example 50 μV or 100 μV. Typically, if the peak signal is greater than the threshold, it is not used for mapping.

A multi-electrode catheter with a central reference electrode can be realized in other ways that are consistent with the disclosed technique. For example, a multi-arm catheter nay comprise such a reference electrode disposed on a distal end of a shaft of the catheter, just proximally to the origin point of the arms. Non-limiting examples of such catheters are described in U.S. Patent Applications Publications 2017/0172442 and 2017/0319144, whose disclosures are incorporated herein by reference.

The rationale behind the above-described technique is that, typically, the baseline level changes by injury current are acquired by a spine electrode, but not by the central electrode. In contrast, baseline level changes that are caused by other factors, such as far-field transmission or local environmental conditions (e.g., from scar tissue), are typically acquired by both electrodes.

In an embodiment, the baseline level of the central electrode, $V_{CRE}$, is measured with respect to a Wilson Central Terminal (WCT) surface electrode configuration described below. (The surface electrodes can also be used to acquire the aforementioned ECGs.) Similarly, the baseline level of a spine electrode, $V_{SE}$, is measured with respect to the WCT set. If $V_{CRE} = V_{SE}$ (within a given tolerance) then it is assumed that no injury current is present, and the signal may thus be accepted for mapping; if $V_{CRE} \neq V_{SE}$ then the presence of injury current is assumed, and the signal is not accepted for mapping.

System Description

FIG. 1 is a schematic, pictorial illustration of a catheter-based electrophysiological (EP) sensing and signal-analysis system 20, according to an embodiment of the present invention. In the embodiment described herein, catheter 21 is used for EP mapping of heart 26. Further, an ECG recording instrument 35 may receive various types of ECG signals sensed by system 20 during the process.

As shown in inset 25, system 20 comprises a catheter 21 having a multi-electrode basket assembly 40 fitted on a distal end of a shaft 22 of the catheter. Shaft 22 of catheter 21 is navigated by a physician 30 into a heart 26 of a patient 28. Physician 30 inserts shaft 22 through a sheath 23, while manipulating shaft 22 using a manipulator 32 near the proximal end of the catheter.

In an embodiment, basket assembly 40 is configured to perform EP mapping of a cardiac chamber of heart 26 obtaining electrophysiological signals from cardiac chamber surfaces 50. Inset 45 shows an enlarged view of basket catheter 40 inside a cardiac chamber of heart 26. As seen, basket catheter 40 comprises an array of electrodes 48 coupled onto spines that form the basket shape. Basket assembly 40 further includes a central reference electrode 58 which is in contact with a blood pool only. The proximal end of catheter 21 is connected to a control console 24, to transmit, for example, electrograms acquired by electrodes 48.

Using reference electrode 58, basket catheter 40 can acquire unipolar electrograms by measuring potential difference between the central electrode of the basket (which does not contact tissue and is assumed to be a local ground) and a spine electrode 48 in contact with the tissue. As described above, a unipolar electrogram acquired by an electrode 48 that exerts too much force on chamber surface 50 tissue may suffer from injury current (e.g., baseline shift) that degrades the signal. The disclosed technique mitigates degradation of an EP map constructed with some of the raw data (the acquired data points) suffering from injury current, as described above and in method FIG. 3.

Console 24 comprises a processor 41, typically a general-purpose computer, with suitable front end and interface circuits 38 for receiving EP signals (e.g., ECGs and EGMs) as well as non-EP signals (such as position signals) from electrodes 48 of catheter 21. The EP signals are stored in a memory 47 of the processor.

To receive EP signals, processor 41 is connected to electrodes 48 via wires running within shaft 22. Interface circuits 38 are further configured to receive ECG signals, such as from a 12-lead ECG apparatus that can be ECG recording instrument 35, as well as non-ECG signals from surface body electrodes 49. Typically, electrodes 49 are attached to the skin around the chest and legs of patient 28. Processor 41 is connected to electrodes 49 by wires running through a cable 39 to receive signals from electrodes 49.

Four of surface body electrodes 49 are named according to standard ECG protocols: MA (right arm), LA (left arm), ML (right leg), and LL (left leg). A Wilson Central Terminal (WCT) may be formed by three of the four named body surface electrodes 49, and a resulting ECG signal, $VW_{CT}$, is received by interface circuits 38.

During an EP mapping procedure, the locations of electrodes 48 are tracked while they are inside heart 26 of the patient. For that purpose, electrical signals are passed between electrodes 48 and body surface electrodes 49. Based on the signals, and given the known positions of electrodes 22 on the patient's body, a processor 28 calculates an estimated location of each electrode 22 within the patient's heart. Such tracking may be performed using the Active Current Location (ACL) system, made by Biosense-Webster (Irvine California), which is described in U.S. Pat. No. 8,456,182, whose disclosure is incorporated herein by reference.

The processor may thus associate any given signal received from electrodes 48, such as EGMs, with the location at which the signal was acquired. Processor 41 uses information contained in these signals (e.g., to annotate EP signals) to construct an EP map, such as a local activation time (LAT) map, to present on a display.

Processor 41 is typically programmed in software to carry out the functions described herein. The software may be downloaded to the processor in electronic form, over a network, for example, or it may, alternatively or additionally, be provided and/or stored on non-transitory tangible media, such as magnetic, optical, or electronic memory. In particular, processor 41 runs a dedicated algorithm as disclosed herein, included in FIGS. 3 and 4, that enables processor 41 to perform the disclosed steps, as further described below.

Although the pictured embodiment in FIG. 1 relates specifically to the use of a basket catheter for cardiac mapping, other distal-end assemblies may be used, such as the aforementioned arcuated Lasso® catheter or the multi-arm Pentaray® catheter. Moreover, the different distal-end assemblies may be further used to perform an electrical ablation.

Baseline Shift in Cardiac Electrophysiological Signals

Figure 2:
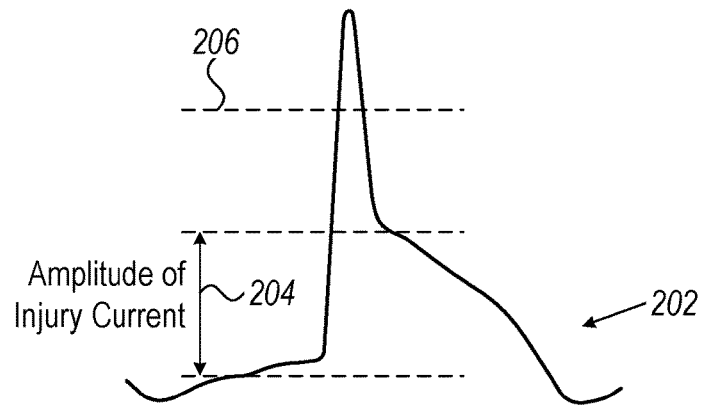
FIG. 2 is a schematic graph of a unipolar electrogram acquired by the system of FIG. 1, which demonstrates a degrading effect of injury current on the electrogram, according to an embodiment of the present invention.

FIG. 2 is a schematic graph of a unipolar electrogram 202 acquired by system 20 of FIG. 1, which demonstrates a degrading effect of injury current on the electrogram, according to an embodiment of the present invention. The plotted waveform is of a potential difference between one of electrodes 48 of catheter assembly 40 and its center reference electrodes 58.

The presence of injury current is manifested as a baseline shift of an amplitude 204 in the unipolar amplitude. This shift causes broadening of the signal. In the shown embodiment, the baseline shift causes the signal to exceed a predefined threshold value 206. This can be used as a criterion to detect and omit from use (e.g., for constructing an EP map) EP signals that were degraded by injury current. For example, a processor can be configured to assume that injury current is present if the acquired EP signal amplitude is greater than the preset threshold 206, for example 50 µV or 100 µV.

Allowing for Injury Current in EP Mapping

Figure 3:
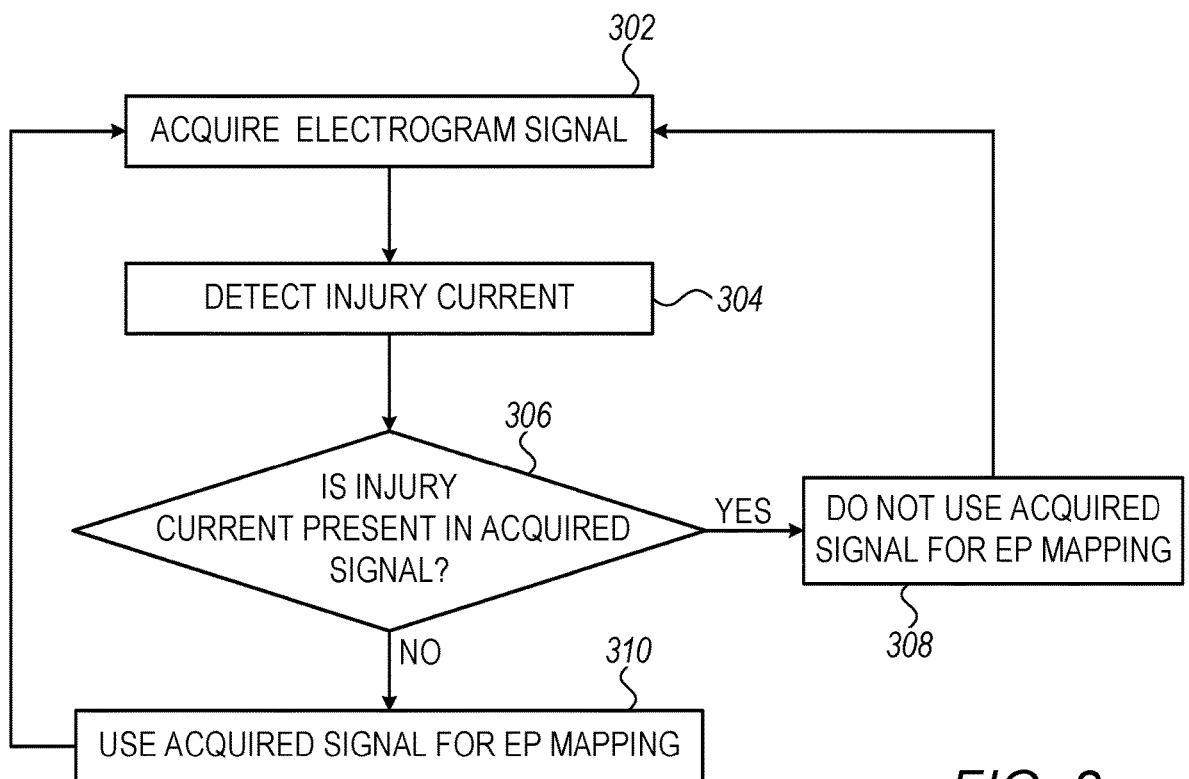
FIG. 3 is a flow chart describing a method to allow for injury current when EP mapping, by detecting and avoiding distorted electrograms, according to an embodiment of the present invention.

FIG. 3 is a flow chart describing a method to allow for injury current when EP mapping, by detecting distorted electrograms and avoiding using them, according to an embodiment of the present invention. The algorithm, according to the presented embodiment, carries out a process that begins with interface circuits 38 receiving an electrogram acquired by catheter 21, at an electrogram acquisition step 302. Next, processor 41 applies an algorithm to detect, by one of the methods described in FIGS. 4 and 5 below, or other methods, if the acquired electrogram suffers from the presence of injury current, at an injury current detection step 304.

At a checking step 306, the processor 41 checks if it has detected an injury current. If the answer is "yes," the processor drops the electrogram from use in an EP map, at a signal dropping step 308. If the answer is "no," the processor uses the electrogram in an EP map, at a signal using step 310. Using the electrogram can mean annotating an LAT value on the electrogram to include a data point in an LAT map.

Figure 4:
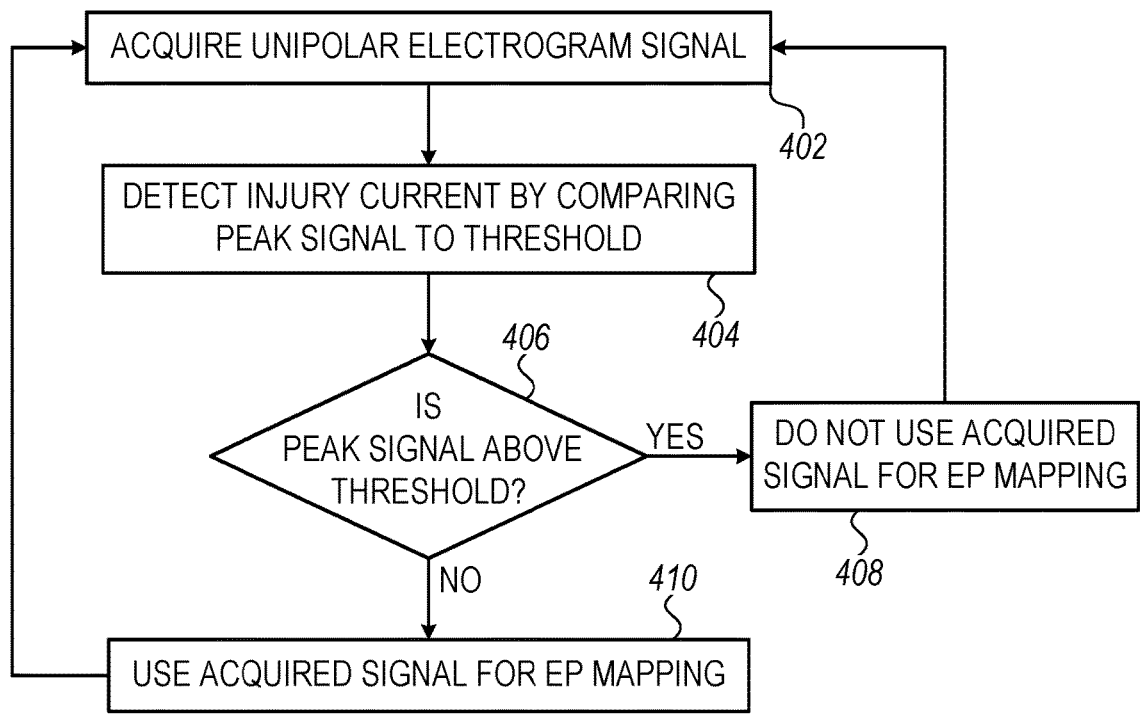
FIG. 4 is a flow chart describing a method for detecting electrograms distorted by injury current by comparing electrogram peak amplitude to threshold, and dropping such electrograms, according to an embodiment of the present invention.

Methods to Detect Presence of Injury Current in Cardiac Electrophysiological Signal FIG. 4 is a flow chart describing a method for detecting an electrogram distorted by injury current by comparing electrogram peak amplitude to threshold, and dropping such electrograms, according to an embodiment of the present invention. The algorithm, according to the presented embodiment, carries out a process that begins with interface circuits 38 receiving a unipolar electrogram acquired by catheter 21, such as electrogram 202, at a unipolar electrogram acquisition step 402. Next, processor 41 applies an algorithm to detect, by comparing peak electrogram signal at a given window of interest (WOI) to threshold 206, if the acquired electrogram suffers from presence of injury current, at an injury current detection step 404.

At a checking step 406, the processor 41 checks if threshold 206 has been exceeded. If the answer is "yes," the processor drops the unipolar electrogram from use in EP map, at a signal dropping step 408. If the answer is "no," the processor uses the unipolar electrogram in EP map, at a signal using step 410. Using the electrogram can mean annotating an LAT value on the electrogram and include that data point in an LAT map and/or in a potential map.

Figure 5:
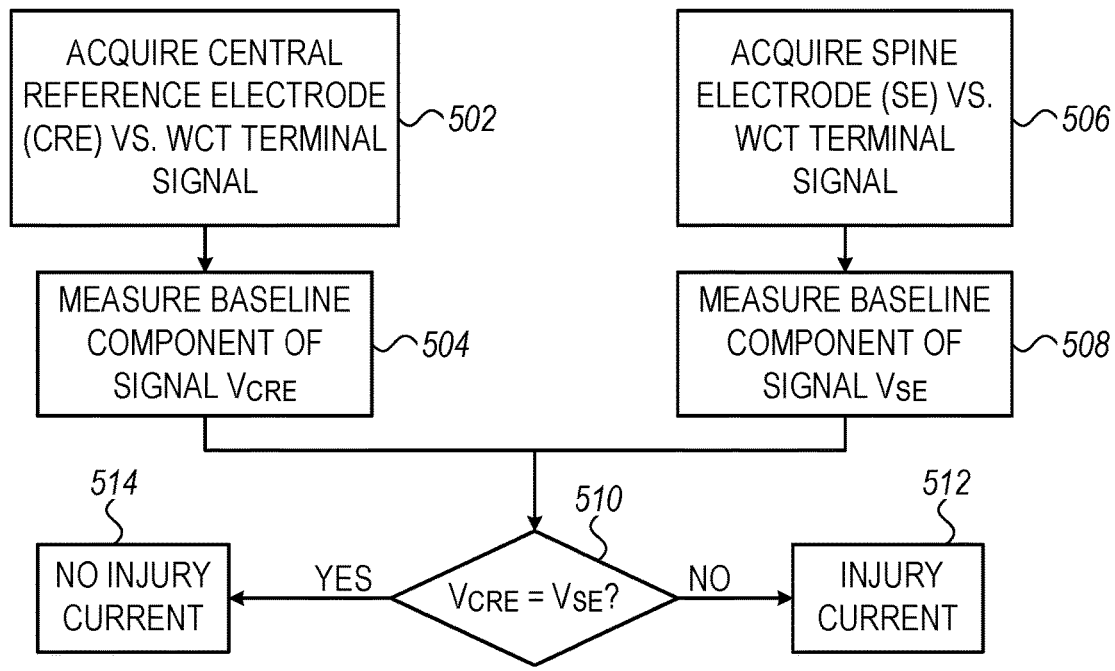
FIG. 5 is a flow chart describing a method for detecting electrograms distorted by injury current by comparing baseline signals, according to another embodiment of the present invention.

FIG. 5 is a flow chart describing a method for detecting an electrogram distorted by injury current by comparing baseline signals, according to another embodiment of the present invention. The algorithm, according to the presented embodiment, carries out a process that begins with interface circuits 38 receiving an EP signal from central reference electrode 58 relative to the WCT terminal described in FIG. 1, at a reference signal acquisition step 502. Next, processor 41 applies an algorithm to measure a baseline potential component $V_{CRE}$ of the signal, at a reference baseline signal measurement step 504.

In parallel, interface circuits 38 receive an EP signal from a spine electrode 48 relative to the WCT terminal, at a tissue signal acquisition step 506. Next, processor 41 applies an algorithm to measure a baseline potential component $V_{SE}$ of the tissue signal, at a tissue baseline signal measurement step 508.

At a baseline signal comparison step 510, processor 41 checks if the two baseline signals are equal (up to a given tolerance). If the answer is "no," the processor indicates (512) that a respective unipolar electrogram signal between electrodes 48 and 58 suffers from a certain level of injury current. If the answer is "yes," the processor indicates (514) that no injury current was detected therein.

The processor may use or drop the respective unipolar electrogram, based, for example, on the condition of step 410, or by comparison ($V_{SE}$-$V_{CRE}$) to a threshold value.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
an interface, configured to receive an electrogram acquired in a heart of a patient; and
a processor, configured to:
estimate a level of injury current present in the electrogram, the electrogram comprising at least two EP signals, wherein one of the at least two EP signals is acquired using a reference electrode configured to be immersed in blood and a surface electrode, and another of the at least two EP signals is acquired using the surface electrode and a sensing electrode configured to contact tissue; and
based on the estimated level of injury current, decide whether to use the electrogram in a subsequent analysis.

2. The system according to claim 1, wherein the processor is configured to use the electrogram when the level of injury current is below a threshold, and to discard the electrogram when the level of injury current is above the threshold.

3. The system according to claim 1, wherein the electrogram comprises a unipolar signal acquired between the reference electrode and the sensing electrode.

4. The system according to claim 1, wherein the processor is configured to estimate the level of injury current by comparing a peak level of the electrogram to a threshold.

5. The system according to claim 4, wherein the processor is configured to annotate a local activation time (LAT) value in the electrogram.

6. The system according to claim 1, wherein the processor is configured to use the electrogram by annotating the electrogram and using the annotation in an EP map.

7. A system, comprising:
an interface, configured to receive at least two EP signals acquired in a heart of a patient by a catheter, wherein one of the at least two EP signals is an electrogram acquired using a reference electrode configured to be immersed in blood and a surface electrode, and another of the at least two EP signals is an electrogram acquired using the surface electrode and a sensing electrode configured to contact tissue; and
a processor, configured to:
using the at least two EP signals, estimate a level of injury current present in an EP signal derived from the at least two EP signals; and
based on the estimated level of injury current, decide whether to use the electrogram in a subsequent analysis.

8. The system according to claim 7, wherein the processor is configured to derive the EP signal by selecting one of the at least two EP signals.

9. The system according to claim 7, wherein the surface electrode is a WCT terminal.

10. The system according to claim 7, wherein the processor is configured to estimate the level of injury current by comparing between at least two of the EP signals.

11. The system according to claim 7, wherein the processor is configured to use the derived EP signal by annotating the derived EP signal and using the annotation in an EP map.

12. The system according to claim 11, wherein the processor is configured to annotate a local activation time (LAT) value in the derived EP signal.

13. A method, comprising:
receiving an electrogram acquired in a heart of a patient;
estimating a level of injury current present in the electrogram, the electrogram comprising at least two EP signals, wherein one of the at least two EP signals is acquired using a reference electrode configured to be immersed in blood and a surface electrode, and another of the at least two EP signals is acquired using the surface electrode and a sensing electrode configured to contact tissue; and
based on the estimated level of injury current, deciding whether to use the electrogram in a subsequent analysis.

14. The method according to claim 13, further comprising using the electrogram when the level of injury current is below a threshold, and discarding the electrogram when the level of injury current is above the threshold.

15. The method according to claim 13, wherein the electrogram comprises a unipolar signal acquired between the reference electrode and the sensing electrode.

16. The method according to claim 13, wherein estimating the level of injury current comprises comparing a peak level of the electrogram to a threshold.

17. The method according to claim 13, further comprising using the electrogram by annotating the electrogram and using the annotation in an EP map.

18. The method according to claim 17, further comprising annotating a local activation time (LAT) value in the electrogram.

19. A method, comprising:
receiving at least two EP signals acquired in a heart of a patient by a catheter;
using the at least two EP signals, estimating a level of injury current present in an EP signal derived from the at least two EP signals, wherein one of the at least two EP signals is an electrogram acquired using a reference electrode immersed in blood and a surface electrode, and another of the at least two EP signals is an electrogram acquired using the surface electrode and a sensing electrode in contact with tissue; and
based on the estimated level of injury current, deciding whether to use the electrogram in a subsequent analysis.

20. The method according to claim 19, further comprising deriving the EP signal by selecting one of the at least two EP signals.

21. The system according to claim 19, wherein the surface electrode is a WCT terminal.

22. The method according to claim 19, further comprising estimating the level of injury current by comparing between at least two of the EP signals.

23. The method according to claim 19, further comprising using the derived EP signal by annotating the derived EP signal and using the annotation in an EP map.

24. The method according to claim 23, further comprising annotating a local activation time (LAT) value in the derived EP signal.

* * * * *